United States Patent
Bond et al.

(10) Patent No.: US 7,312,305 B2
(45) Date of Patent: *Dec. 25, 2007

(54) TUMOR CYTOTOXICITY INDUCED BY MODULATORS OF THE CXCR4 RECEPTOR

(75) Inventors: Vincent C. Bond, Stone Mountain, GA (US); James Lillard, Smyrna, GA (US); Ming Bo Huang, Atlanta, GA (US); Harvey Bumpers, Stone Mountain, GA (US); Michael Powell, Douglasville, GA (US)

(73) Assignee: Morehouse School of Medicine, Atlanta, GA (US)

( * ) Notice: Subject to any disclaimer, the term of this patent is extended or adjusted under 35 U.S.C. 154(b) by 409 days.

This patent is subject to a terminal disclaimer.

(21) Appl. No.: 10/392,324

(22) Filed: Mar. 20, 2003

(65) Prior Publication Data

US 2004/0037825 A1    Feb. 26, 2004

(51) Int. Cl.
*C07K 4/02*    (2006.01)

(52) U.S. Cl. .......................................... 530/328; 514/15
(58) Field of Classification Search ................ 530/328, 530/300, 350; 514/15
See application file for complete search history.

(56) References Cited

U.S. PATENT DOCUMENTS 5,221,610 A * 6/1993 Montagnier et al. ......... 435/7.1

* cited by examiner

*Primary Examiner*—Stephen L. Rawlings
(74) *Attorney, Agent, or Firm*—Glenna Hendricks

(57) ABSTRACT

The present invention provides a means of selectively killing epithelial cell carcinomas by administering a CXCR4-specific sequence of the Gp120 protein or Nef proteins or the proteins themselves (the modulators) such as that found in strains HIV-1, HIV-2, SIV, or FIV CXCR4-specific Gp 120 sequences or Nef proteins or sequences may be delivered to the mucosa or systemically. The mucosal means of application include oral, intranasal, ocular, intravaginal, rectal, and/or intraurethral administration in liquid or particulate form.

6 Claims, No Drawings

TUMOR CYTOTOXICITY INDUCED BY MODULATORS OF THE CXCR4 RECEPTOR

FIELD OF THE INVENTION

This invention relates to the use of envelope protein (Gp 120) and Nef proteins of Human Immunodeficiency Virus type 1 (HIV-1), HIV-2, Simian Immunodeficiency Virus (SIV), Feline Immunodeficiency Virus (FIV) and peptides of these proteins (modulators) as therapeutic agents against epitheial carcinomas. The useful peptides and proteins are referred to herein as modulators.

BACKGROUND OF THE INVENTION

Despite recent advances in cancer research, the development of cancer cell-specific therapies has remained elusive. This "targeted approach" should ideally reduce the side effects due to the toxicity towards normal cells, while increasing the specificity to the cancer cells. There are a limited number of targeted cancer therapies. For example, antisense therapy works at the molecular level to stop the process by which cancer-causing proteins are produced by host tumor cells. Gene therapy involves development of delivery systems to deliver a therapeutic gene into cancer cells. These molecular treatments theoretically will result in (i) increased sensitivity of cancer cells to a specific drug; (ii) replacement of damaged genes that cause tumorigenesis, metastasis, and angiogenesis; (iii) enhanced immune detection. To date, therapies actually providing such benefits using gene therapy have not been achieved.

Chemotherapy is the traditional approach to cancer treatment. Advances in biotechnology have promoted the development of better (e.g., targeted) drugs with fewer side effects. While promising, these molecular biology-based therapies require complex delivery systems, and protocols that are both difficult to practice and are excessively costly. The further improvement of cancer treatments requires a better understanding of the components that make up cancer cells.

All cells have surface receptors that work in concert with associated proteins to signal and cause host cell activities. For example, the epidermal growth factor receptor helps control cell growth, repair and metastasis. Many tumor cells have been found to have higher numbers of epidermal growth factor receptors than normal cells. Cetuximab (IMC-225) was specifically designed to target and block epidermal growth factor receptors preventing cell division and repair during rapid growth.

Unfortunately, not all carcinomas have high numbers of epidermal growth factor receptors. Other targeted therapies have presented similar problems. Recently, the FDA approved the first targeted cancer therapy drug, Herceptin (trastuzumab), a monoclonal antibody used to treat metastatic breast cancer. By blocking a protein called HER-2, cancer cell growth was stopped. HER-2 is a factor in about 25 to 30 percent of breast cancers. While other targeted cancer therapies are being developed, there will certainly not be one target, nor one therapy that stops or kills all tumors. Consequently, the development of therapies to exploit newly identified specific targets associated with tumor proliferation will be required.

The cloning of the retroviral nef genes has been taught and some functions (but not anti-carcinoma properties) have been taught in U.S. Pat. No. 6,020,171 of Saito, et al, issued Feb. 1, 2000, which is incorporated herein by reference in its entirety.

SUMMARY OF THE INVENTION

The present invention provides a means of selectively killing epithelial cell carcinomas by administering a CXCR4-specific sequence of the Gp 120 protein or Nef proteins or the proteins themselves (the modulators) such as that found in strains HIV-1, HIV-2, SIV, or FIV CXCR4-specific Gp 120 sequences or Nef proteins or sequences may be delivered to the mucosa or systemically. The mucosal means of application include oral, intranasal, ocular, intravaginal, rectal, and/or intraurethral administration in liquid or particulate form. Systemic means of application include parenteral, intravenous, or intramuscular administration in liquid or particulate form. The active agents may be also be administered using targeting liposomes, microspheres or solid supports.

DETAILED DESCRIPTION OF THE INVENTION

Chemokines and CXCR4

Chemokines are a superfamily of small, cytokine-like proteins that induce cytoskeletal rearrangement, firm adhesion to endothelial cells and directional migration through interaction with G-protein-coupled receptors. The chemokine receptor/chemokine ligand, CXCR4/SDF-1a, is a unique chemokine receptor-ligand pair in that (i) the receptor is required in development (CXCR4 knockouts in mice are developmentally lethal), and there is only one identified ligand for this receptor (SDF-1a, knockouts of which are developmentally lethal); (ii) the CXCR4 receptor has been shown to be a co-receptor for the Human Immunodeficiency Virus (HIV-1).

CXCR4 has been shown to be highly expressed by human breast carcinoma cells, and skin melanomas. It has been found that primary, or normal epithelial cell types: i.e., normal cells from which tumors (mammary epithelial cells, and melanocytes respectively) normally lack expression of the CXCR4 receptor. Expression of this chemokine receptor on the cell surface appears to promote metastasis by acting directly on tumor cell migration and invasion.

The chemokine receptor/chemokine ligand, CXCR4/SDF-1a have also been shown to be critically involved in a growth factor-regulated signaling system in endothelial cells that mediates important steps in postnatal vascular remodeling postnatally. Vascular remodeling or angiogenesis is a critical step in the establishment and subsequent fitness of tumors. Development of antagonists for the CXCR4 receptor presents a useful means for interfering with tumor progression and metastasis.

HIV-1 Gp120—Modulator

There is extensive literature on HIV-1 envelope-induced apoptosis. A Gp 120-induced effects on endothelium, including apoptosis, have been observed as recorded herein. It has now been found that the observed Gp 120-induced effects are mediated through the CXCR4 receptor. This has been shown by using competition assays with CXCR4 or CCR5 antibodies, or the respective ligands for each receptor. Many studies have addressed cell killing of uninfected lymphocytes through apoptotic mechanisms that were mediated by the HIV-1 envelope.

In accord with the teachings herein, the affects of Gp 120 and sequences therefrom through the CXCR4 receptor, which is expressed by epithelial carcinomas and vascular endothelium, show that this modulator will act to selectively kill tumor cells, while effacing deleterious effects on the normal epithelium, and will act on vascular remodeling of the tumor. Compositions containing the Gp 120 modulator in cancer cell apoptotic-enhancing amounts may advantageously be administered at therapeutic levels as treatment for cancer. For example, dosages such as 1 to 10 ηg in small animals and from 10 micrograms to 10 milligrams in large mammals may be administered. These agents may be administered in the usual pharmaceutical carriers such as saline, buffered saline, glucose, etc. Such compositions may be provided as capsules, tablets, inhalants, sprays, or as liquids or gels for topical application. The modulators may also be administered using a solid supports such as a sponges or fiber materials and targeted liposomes and microspheres as a carriers. Compositions for oral ingestion may be enteric coated or administered on carriers such as microspheres to provide controlled release.

The envelope proteins of HIV-2, Simian Immunodeficiency Virus (SIV), and Feline Immunodeficiency Virus (FIV) are very similar to the t-tropic Gp 120 protein of HIV-1 in some respects. All have been shown to have variants that interact with the CXCR4 receptor, and in some cases to compete for binding with HIV-1 Gp 120 IIIb. Thus, these variants could be used to induce a similar effect on tumor cells. Soluble HIV-1 Gp 120 protein has been taken through clinical trials as part of the HIV/AIDS vaccine program. These trials show that, in short/acute exposures, this protein appears not to cause any overt effects in healthy volunteers. The teachings herein further describe these modulators for use in short and limited pulsed exposures.

HIV-1 Nef-modulator

It has been suggested that extracellular Nef protein induces cell death in uninfected cells. A number of Nef-induced effects have been observed (not requiring nef antibodies) have been on endothelium and epithelium, including apoptosis. In studies conducted during study of the invention, it was found that nef-induced effects are mediated through the CXCR4 receptor. This has been shown by using competition assays with CXCR4 or CCR5 antibodies or their respective ligands for each receptor.

Materials and Methods

Proteins and Antibodies

The Gp120 protein, which was obtained from Intracel (Issaquah, Wash.; Cat.#12001), is the IIIB variant, and was measured to be >90% pure as estimated by Coomassie blue gel staining. Gp120 was expressed from a baculovirus expression system, and is full length, and glycosylated. RANTES, and SDF-1a were human receptor ligands obtained from Chemicon (Temecula, Calif.). The following antibodies were used: Monoclonal mouse anti-human fusin clone 12G5, mIgG2a[CXCR4] (RDI Cat # RDI-FUSIN-Nabm, Research Diagnostics Inc, Pleasant Hill Road, Flanders N.J. 07836); ImmunoPurer Goat Anti-rabbit IgG (H+L), Peroxidase Conjugated; rabbit anti-HIV-1 Nef antiserum (NIH AIDS Research and Reference Reagent Program, CAT #2949), Polyclonal (Rabbit) anti-CXCR4 antibody (ABR Cat.# OPA1-01101); Monoclonal (Mouse) anti-CCR5 antibody (PharMingen, Cat.# 36461A); Monoclonal (Mouse) anti-CD4 antibody (American Bio-Technologies, Inc., Cat.#003101). Ceramide was obtained from RBI (Natick, Mass.).

The nef protein was expressed and purified in the inventors' laboratory. overlapping 20 mer peptides encompassing the entire nef protein and overlapping 15 mer peptides encompassing the entire gp 120 protein were obtained from the NIH AIDS Research & Reference Reagent Program (McKesson HBC BioServices, MD) Other specific peptides designed from within gp 120 or nef were obtained from SigmaGenosys.

Cell Cultures

Normal human mammary epithelial cells (Biowhittaker, Walkersville, Md.) were grown in MEGM BulletKit (Biowhittaker, Walkersville, Md.), ReagentPack (Biowhittaker, Walkersville, Md.). Normal human vascular endothelial cell (HUVEC) (Biowhittaker) were grown in endothelial cell growth medium (EGM). The medium was supplemented with 10 ηg/ml human recombinant epidermal growth factor (hEGF), 1.0 µg/ml hydrocortisone, 50 µg/ml gentamicin, 50 µg/ml amphotericin B, 12 µg/ml bovine brain extract (BBE) and 2% v/v fetal bovine serum (FBS).

Breast lines MDA-MB-468 (ATCC # HTB-132) were grown in Leibovitz's L-15 with 2 mM L-glutamine, 90%; Fetal Bovine Serum, 10%. MDA-MB-231 (ATCC # HTB-26), grown in RPMI 1640 medium containing fetal bovine serum 10%. MCF7 (ATCC # HTB-22), grown in minimum essential medium Eagle with 2 mM L-glutamine and Earle's BSS adjusted to contain 1.5 g/L of Sodium bicarbonate, 0.1 mM non-essential amino acids, 1.0 mM sodium pyruvate supplemented with 0.01 mg/ml bovine insulin, and containing Fetal bovine serum, 10%. DU4475 (ATCC # HTB-123) were grown in RPMI 1640 medium with 5 ml of Penicillin-Streptomycin-Glutamine, and adjusted to contain 1.5 g/L Sodium bicarbonate, 4.5 g/L Glucose, 10 mM HEPES, 1.0 mM Sodium pyruvate, with Fetal bovine serum, 10%. Media was removed, cultures rinsed with 0.25% Trypsin, 1 mM EDTA solution (GIBCO BRL, Cat # 25200072) for 5 to 10 min at RT, and spun at 2000 rpm for 15 min. The solution was removed, fresh culture medium added, and cells dispensed into fresh culture flasks. Cultures were incubated at 37° C. with 5% $CO_2$ for two to four days.

Colon lines SW480 (ATCC #CCL-228) were grown in Leibovitz/s L-15 with 2 mM L-glutamine and 10% FBS. HT-29 (ATCC #HTB-8) was grown in McCoy's 5a medium with 1.5 mM L-glutamine and 10% FBS. The human prostate cell lines LNCaP (a lymph note metastatic line), primary prostatic tumor cell line CWR22, Lung metastatic line PC-3 and brain metastatic line DU145 were also cultured.

Apoptosis, Terminal Deoxynucleotidyl Transferase dUTP Nick-end Labeling (TUNEL) Assay Apoptosis generates DNA free ends which can be labeled in situ using terminal deoxynucleotidyl-transferase (TdT), incorporating an exogenously added labeled nucleotide to the DNA strand. This label can then be visualized directly by fluorescence or indirectly using anti-FITC-peroxidase, and a calorimetric assay. Cells on coverslips were washed with PBS, and fixed for 30 minutes at RT with 4% paraformaldehyde, in PBS, pH 7.4. They were then washed with PBS, and permeabilized with 0.1% Triton X-100 for 10 minutes at room temperature (RT). The slides were rinsed twice with PBS, and air dried for 2 minutes. The manufacturer's procedure for TUNEL staining the slides was followed (manufacturer's procedure for the In Situ Cell Death Detection Kit, AP; Boehringer Mannheim, Indianapolis, Ind.). Total cell counts were determined by counterstaining fixed cultures with 20 µg/ml of Hoechst 33258. All specimens were observed by epifluorescence on a computer-controlled microscope system based on a Zeiss Axioskop microscope (Carl Zeiss, Thornwood, N.Y.), and the images were obtained and examined using a charged coupled device (CCD) camera, MagnaFire, model S99806 (Olympus American, Melville, N.Y.). Images were examined using Image-Pro Plus 4.1 for Windows (Media Cybernetics, Silver Springs, Md.) software.

Competition Assays

Cultures ($2.5 \times 10^5$ cells/dish) were incubated for 24 to 48 hours. Cultures were then pretreated with the appropriate antibody for 30 min. at room temperature (RT). Cultures were subsequently washed with PBS and then treated with the modulator for 24 hours. Finally, slides were stained and imaged as described above.

Immunocytochemical Assay

Cultures were rinsed 2× with 1×PBS containing 0.1% glycine to reduce intrinsic fluorescence. They were blocked with 1% Goat serum in PBS containing 0.3% Triton X-100 at RT for 1 hr. Primary antibody (1:250) was added to the blocking solution, and the slides were incubated overnight at 4° C. The slides were rinsed 3× with 1×PBS containing 1% Triton X-100 at RT, and the second antibody (1:200) (Texas Red Anti-Mouse IgG [H+L], Vector Cat. # TI-2000, 1.5 mg/bottle) was added in the blocking solution and incubated at RT for 1 hr. The slides were then rinsed 3× with 1×PBS containing 1% Triton X-100 at RT, and fixed in 4% paraformaldehyde at RT for 60 min. Finally, they were rinsed 3× with 1×PBS, briefly dried, mounted with mediamowoil, excess oil removed and slides were visualized or stored in the refrigerator. Slides were observed by epifluorescence on a computer controlled microscope system based on a Zeiss microscope, and a CCD camera as described above. Images were subsequently examined as described above.

Cloning and Expression of HIV-1, HIV-2 and SIV Nefs

To clone and express proteins from HIV-1, HIV-2 and SIV, the Nef reading frames of each virus were amplifed by PCR from full length viral clones and placed into the expression vector pcDMA 3J/V5-His TOPO (Invitrogen). The HIV-1 viral clone used was pNL4-3 (gift of Eric Freed, NIH), the HIV-2 clone was from the JK strain (HIV7312A, gift of John Kappes, University of Alabama, Birmingham) and the SIV clone was from SIV mac239 (p239SpE3' nef Open, AIDS reagent program, cat #2476). The primers used to amplify the nef reading frame from pNL3-4 were: forward 5'-CCT AGA AGA ATA AGA CAG GGC (Seq. I.D. No. 1) and reverse 5' CAC TAC TTG AAG CAC TCA AGG C (Seq. I.D. No. 2). The primers used to amplify the nef reading frame from SIV p239SpE3' were, forward, 5'-CCT CTT CAG CTA CCA CCG CTT GAG AGA CTT ACT C (Seq. I.D. No. 3) and, reverse, 5' TGA CTA AAA TGG TCT GAG G (Seq. I.D. No. 4). The primers used to amplify the nef reading frame of HIV-2 were, forward, 5' GAA GAA GGA GGT GGA AAC GAC G (Seq. I.D. No. 5) and, reverse, 5'-AAG TGC TGG TGA GAG TCT AGC (Seq. I.D. No. 6). After PCR amplification, each PCR product was inserted into the vector by TOPO cloning according to the manufacturer's instructions. The sequence of each clone was confirmed by dideoxy sequencing. The functionality of each clone was verified by its ability to trans complement a nef-deleted strain of NL4-3 and restore infectivity as determined by MAGI infectivity assays.

To express the desired protein, 6 μg of each plasmid was separately transfected into HEK 293 cells using Effectene reagent (Qaigen). The Effectene was removed after 6 hours and fresh medium was added. After 48 hours, the supernatants were collected and spun at 400× g to remove any cellular debris. Supernatants were either used immediately or frozen at −80° C. until use.

Apoptosis Assay: Agarose Gel Electrophoresis/DNA Fragmentation

Untreated or treated cells were collected, and DNA was harvested from normal or cancer cell cultures. Briefly, the cells were washed with PBS, pelleted at 1600 g for 20 minutes at 4.degree. C., and resuspended in 50 mM Tris-HCl, pH 7.5, 20 mM EDTA buffer at about $10.\text{sup}.7$ cells/ml. The cells were then treated 2.times. with lysis buffer: 1.0% NP-40 (Sigma, St. Louis, Mo.) in the same Tris/EDTA buffer at RT for 2 minutes followed, by centrifugation at 1600 g for 5 minutes. After the last spin, SDS was added to the supernatant to 1% final concentration, RNase A (Sigma, St. Louis, Mo.) was added to 5 mg/mil final concentration, and the solution incubated at 56.degree. C. for 2 hours. Subsequently, protease K (Promega, Madison, Wis.) was added to the solution to 2.5. .mu.g/ml and incubated at 37.degree. C. for 2.5 hr. Ammonium acetate was added to 4 M final concentration, 0.7 volumes of isopropanol was added, the solution was put at −20.degree. C. overnight followed by centrifugation at 14,000 rpm for 30 minutes. The pellets were washed twice with 70% ethanol, dried and resuspended in 10 mM Tris-HCl, pH 7.5, mM EDTA. DNA samples, 18 .mu.g per condition, were prepared in neutral loading buffer to a final concentration of 0.02% bromophenol blue, 5% glycerol, 0.1% SDS, and 50 .mu.g of ethidium bromide, loaded onto a neutral agarose gel (1.7%), and run at50V for 2.5 hours. DNA size standards were HindIII digested lambda DNA, and DNA ladder markers (Promega, Madison, Wis.). The resultant separated bands were visualized and photographed using a kodak™ Eloctrophoresis Documentation and Analysis System 120 (Eastman Kodak Company, Rochester, N.Y.) with a Fotodyne™ transilluminator UV box.

Transfection Assay

MDA-MB-468 cells in log phase were transfected with 1 or 2.5 microg of pCXCR4 and 8 microg of GFP vector (transfection control) or with 2.5 microg of PCR 3.1 vector and 8 microg of GFP vector as negative controls. The aliquots were transferred to 0.4 cm electroporation curvette and electroporated with 0.25 kV. 950 μF capacitance pulse and 200 ohms resistance. Cells were then allowed to sit a room temperature for 10 minutes, then transferred to a microfuge tube containing 400 ml RPMI and centrifuged at 3000 rpm for 5 minutes to remove debris. The cell pellet was resuspended in 1 ml of RPMI containing serum and incubated overnight or 16 hours at 37° C. in 6-well plates to allow expression of the transfected gene.

In assays examining effect of the Gp 120 blocking on apoptosis, the transfected cell pellets were exposed to 6 μg of anti-gp120 antibody in 200 μl of HUVEC culturing medium at 37° C. for 1 hour. This solution was then diluted into 1 ml of HUVEC culturing medium and layered onto the HUVEC monolayers.

Animal Studies

Transplantation and tumor measurement in mice:

Male CB, 17 SCID mice, aged 5 to 6 weeks, were housed in horizontal laminar flow cabinets free of microbial pathogens. Mice were obtained at age 1 month and quarantined for at least 1 week before inoculation. Mice (5 per group per study) were injected with at least $10^6$ epithelial cells (the prostate, colon, breast cell lines as identified below) in 0.1 ml phosphate buffered saline (pH 7.4) or Hank's Balanced Salt Solution (HBSS) subcutaneously into the bilateral flank region over the right hip. Mice were then housed and monitored over time for tumor formation. The animals tolerated the procedures without incident and none died due to technique or infection. Tumors were routinely monitored for tumor implantation, propagation and metastasis. All tumor volumetric measurements were done in 3 dimensions in cubic centimeters using an engineer's caliper.

Cell lines injected included breast epithelial tumor lines DU4475, MDA-MB-648, colon epithelial tumor lines SW480 and HT-29, human prostate cell lines LNCaP (a lymph note metastatic line), primary prostatic tumor cell line CWR22, Lung metastatic line PC-3 and brain metastatic line DU145.

Sample and Tissue Collection:

Mice were euthanized by cervical dislocation. Tumor areas identified and measured previously in mice sere examined for tumor tissue. Tumor was then taken for histological studies or reimplementation according to usual protocols.

Analysis of Data

SigmaPlot 2000™ (Chicago, Ill.), a statistical analysis program, was used to compile the data. The data were subsequently analyzed by the Student's t-test, using a two-factor, unpaired test. In this analysis, data gathered using the various treatment conditions were compared to those gathered in the untreated control conditions. For this study, significance, or lack of significance of the data was set at: p <or>0.01, respectively.

Initial Analysis of Modulator Effect in an in Vitro Epithelial line Culture Model Using a series of breast carcinoma cell lines as well as primary mammary epithelial cells expressing various levels of the CXCR4 receptor, the antagonistic/killing effects of the modulators in these cells were studied. The modulators selectively induced apoptosis in cells expressing the CXCR4 receptor, but had no effect on cells not expressing that receptor (e.g., normal primary epithelium). Further, the amount of induced apoptosis was directly proportional to the relative amount of CXCR4 expressed by those cells. The HIV-1 Gp120 JR-FL variant, a macrophage-tropic variant that acts through the CCR5 receptor, had no effect on any of these cell lines. Antibodies to the CXCR4 receptor were shown to block the apoptotic effect of the modulator, where antibodies to CCR5 or CD4 had no effect on modulator-induced apoptosis. The natural ligand of CXCR4, SDF, had no similar effect on the carcinoma cell lines. This clearly indicates that the modulator uniquely induces apoptosis in epithelial carcinomas through the CXCR4 receptor expressed at varying levels on these carcinoma lines, but does not kill normal epithelial cells.

The effect of the modulator (Gp120 IIIb) on four breast carcinoma cell lines, as well as normal primary mammary epithelium was studied. The cell lines were selected based-on their expression levels of the CXCR4 receptor mRNA. It was found that (i) Primary normal mammary epithelial cells, or MDA-MB-468 expressed no CXCR4 receptor RNA, (ii) MCF7 expressed low levels of CXCR4 mRNA, (iii) MDA-MB-231 expressed medium levels, and (iv) DU4475 expressed very high levels of the receptor mRNA. The primary mammary epithelial cells were shown to lack expression of CXCR4 mRNA.

The levels of CXCR4 in these cell types was confirmed using immunocytochemical analysis (ICA) as a tool to perform a semi-quantitative, relative measurement of the amounts of CXCR4 protein on the cell surface of each cell type. Cells were grown on coverslips, and stained unfixed (which only stains CXCR4 on the cell surfaces) using a monoclonal antibody for CXCR4, and a secondary Texas Red goat antimouse antibody. Cultures were imaged by confocal microscopy, and the intensity of staining on the cultured cell surfaces was measured from the images using Image-Pro 5.0 software. It was found that the relative amount of surface labeling of CXCR4, when comparing the five cell types examined, was directly proportional to their mRNA levels. Thus, primary normal mammary epithelial cells, and MDA-MB-468 showed no CXCR4 staining on the cell surface. Alternatively, both MCF7 and MDA-MB-231 displayed medium levels of CXCR4 staining on the cell surface, with the levels observed with MCF7 being somewhat less than those displayed by MDA-MB-231. Finally, DU4475 displayed the highest levels of CXCR4 staining.

Each of these cell lines was exposed to the soluble modulator, at varying concentrations from 10 ηg/ml to 100 ηg/ml. The modulator selectively induced apoptosis in cells expressing the CXCR4 receptor (ii, iii, iv), but had no effect on cells not expressing that receptor (i). This apoptosis was a function of the relative amount of CXCR4 expressed by those cells. It was found that the tumor cells expressing the most CXCR4 (DU4475) were killed most effectively, and at the lowest concentrations of the modulator. Alternatively, the normal primary mammary epithelial cells were not affected by any concentration of the modulator. Thus it was shown that the modulator induces cell killing/apoptosis in the tumor cells through the CXCR4 receptor. The amount of apoptosis induced in these tumor cells is directly proportional to the amount of CXCR4 receptor on the cell surface. The modulator has no effect on normal mammary epithelial cells.

Specificity of Modulator for CXCR4-Further Evidence

Further evidence of modulator (Gp120) induced apoptosis in the CXCR4 expressing cell lines was gathered from gel electrophoresis of purified DNA from untreated and modulator-treated cultures. Cultures were either untreated, treated for 24 hours with 10 ηg/ml of the modulator, or with 10 mM (6.35 mg/ml) ceramide. Ceramide at that concentration has been shown to cause apoptosis, and the DNA laddering band pattern suggestive of apoptosis. Subsequently, chromosomal DNA was extracted from these cultures, and separated using neutral gel electrophoresis. The resulting agarose gels were visualized for the laddering band pattern suggestive of internucleosomal cleavage caused by apoptosis. As expected, in the positive control ceramide treated cultures, DNA laddering characteristic of apoptotic cells was observed when compared to the negative control DNA from the untreated cultures. In the modulator-treated cultures of MDA-MB-231, MCF7, and DU4475, DNA laddering was observed. Alternatively, in the modulator exposed cultures of MDA-MB-468 and the primary mammary epithelial cells there was no evidence of DNA laddering, with the electrophoretic pattern looking like the untreated negative control.

The Gp120 JR-FL variant, a macrophage-tropic Gp120 variant that interacts predominantly with the CCR5 chemokine receptor, had no effect on any of these cell lines. Monoclonal or polyclonal antibodies to the CXCR4 receptor blocked the apoptotic effect of Gp120 IIIb. Alternatively, antibodies to CCR5 or CD4 had no blocking effect on modulator-induced apoptosis. The natural ligand of CXCR4, SDF-1, had no similar apoptotic effect on any of the carcinoma cell lines. Finally, a significant reduction, essentially to background levels, in the percentage of apoptotic cells was observed when the Gp120 protein solution was pre-treated with an anti-Gp120 antibody, and this antibody-treated protein solution was subsequently used to treat cultures of MDA-MB-231 cells. Alternatively, mouse IgG had no effect on Gp120-induced increases in apoptosis in the cultures. This evidence clearly shows that the modulator (i.e., Gp120 IIIb) uniquely induces the apoptotic affect through the CXCR4 receptor expressed on these carcinoma lines.

MDA-MB-468 cells, which do not express CXCR4 and are refractive for modulator-induced apoptosis were transfected with pCXCR4 and GFP vector (transfector control), or with PCR 3.1 vector and GFP vector as negative controls. These cells were then either assayed for CXCR4 expression or exposed to modulator for 24 hours. It was observed that CXCR4 expression on the MDA-MB-468 cells correlated directly with modulator induction of apoptosis. All of the observations lend strong evidence of modulator-induced apoptosis in those cell lines expressing CXCR4, with no apoptosis induced in the exposed cells which did not express CXCR4.

HIV Nef as a Modulator

Nef-induced apoptotic effects have been observed on endothelium and epithelium. Both MDA-MB-231 cells or HUVEC cells were treated with various concentrations of purified bacterially-expressed Nef protein. Subsequently, the cultures were either (1) analyzed for chromatic condensation and nuclear fragmentation by phase contrast microscopy, (2) assayed for apoptosis by TUNEL in connection with immunofluorescence microscopy, or (3) analyzed by agarose gel electrophoreses for DNA laddering. Substantial chromatic condensation and extensive nuclear fragmentation was observed in cells exposed to exogenous NEF protein. In dose response/TUNEL assays using different concentration of Nef, there was a clear dosage dependence of Nef protein and apoptosis. Alternatively, in time response/Terminal dUTP Nick End Labeling (TUNEL) assays there was a clear and direct relationship between the time of Nef exposure and the amount of induced apoptosis. Finally, Nef protein exposure induced considerable DNA laddering, as measured by agarose gene electrophoresis/DNA fragmentation analysis.

It was also found that the observed Nef-induced apoptosis is mediated through the CXCR4 receptor. Apoptosis has been shown in CXCR4 expressing tumor epithelial lines and HUVECs, with no effect observed in cells types not expressing CXCR4 (MDA-MB-468, primary breast epithelial cells). Further studies performed indicating the specificity of Nef for the CXCR4 receptor included (1) competition assays with CXCR4 or CCR5 antibodies or the respective ligands for CXCR4 or CCR5 receptor as described above and (2) CXCR4 transfection assay with MDA-MB 468 cells, as described above. All evidence points towards Nef protein as a modulator protein.

The cloned Nef cDNA from HIV-1, HIV-2 and SIV were separately transfected into HEK 293 cells. After 48 hours the conditioned medium was collected from the transfected cultures and spun at 400×g to remove any cellular debris, These conditions supernatants were shown to contain the respective Nef protein (HIV-1, HIV-2 and SIV) by Western Analysis. Interestingly, these conditioned supernatants were shown to have all the apoptotic properties described above for the bacterially expressed HIV-1 Nef protein. Thus, HIV-2 Nef and SIV Nef protein were shown to have similar modulator properties.

Gp120/Nef Peptides as Modulators all of the results described above that were modulator-induced have also been shown to result from use of a number of peptide sequences identified in either the gp 120 or Nef proteins. Overlapping peptide sets obtained from the AIDS Reagent Bank were used in the apoptotic assay as disclosed above. Specific pg 120 and Nef peptides within those sets were identified as inducing apoptosis in epithelial tumor cell lines, as well as in HUVECs. Alternatively, these same peptides had no effect in primary mammary epithelium or in MDA-MB-468 tumor lines. Similar studies to those described above (e.g., anti-CXCR4 competition, MDA-MB-468 transfections with the CXCR4 cDNA clone) were used to show that all peptides identified have apoptotic properties which exert their activity through the CXCR4 receptor.

Peptide Sequences

Nef: Within the Nef protein, a motif spanning amino acids 50-60 from the N-terminus of the protein (NAA-CAWLEAQ) (Seq. I.D. No. 7) was found to have apoptotic/modulator properties. The 10 mer peptide spanning this 50-60 motif was made by standard methods and was found to induce almost 100% of the apoptosis observed for the full Nef protein at an equivalent molar ration (10 mer peptide is 5% the amount used when studying the full protein). Similarly, this same 10 mere sequence, with amino acids randomly scrambled into the sequence ALAETCONAWA (Seq. I.D. No. 8) lost all apoptotic effects, suggesting sequence specificity of this motif.

Gp120: Within the Gp 120 protein, one apoptosis-inducing motif within the V3 loop was identified spanning amino acids 315 to 321 (sequence GRAFYTT) (Seq. I.D. No. 9). A second large apoptosis-inducing region within the C2 region was identified spanning aa 252-280 (STOLLLNGSLAEEEVVIRSENFTDNAKTIIV) (Seq. I.D. No. 10). A 9 mer peptide spanning amino acids 315-324 of gp 120 (GRAFYTTKY) (Seq. I.D. No. 11) was designed and found to induce about 60% of the apoptosis observed from the full gp 210 protein at an equivalent molar ration (9 mer peptide is 2% of the full protein).

Modular Induction of Apoptosis in Endothelium

The effects of Gp 120 (IIIb variant) on endothelium was studied. Using HUVEC's as a model, it was shown that the soluble Gp 120/IIIb protein induced apoptosis. Using competition assays with either CXCR4 or CCR5 antibodies, or their respective natural ligands, it was shown that apoptotic effect could be induced through the CXCR4 chemokine receptor. It was also shown that soluble Gp 120 IIIb-induced apoptosis involves protein kinase-C (PKC), and that phorbol ester stimulated the CXCR4 endocytosis pathway, with the Gp 120-induced PKC induction and the gp 120-induced apoptosis in HUVECs being found to be insensitive to pertussis toxin. This suggests that the endocytosis step is involved in these viral protein induced effects and that activation of the natural ligand (SDF-1a) mediated signaling pathway is not involved in Gp 120-induced apoptosis. It further indicates clear differences in effects of modulator/receptor interactions versus natural ligand/receptor interaction versus phorbol ester/receptor interaction. Similar apoptotic effects were observed for the Nef protein as well as for the Gp 120 and Nef peptides described above.

Modulator Induced Tumor Cytotoxicity in Mouse Tumor Model

Mice injected with prostate tumor lines

SCID mice were injected with several prostate tumor lines. Tumors appeared at about 4-6 weeks post-injection. Once tumor growth was confirmed by observation, one group of 5 mice were injected with a modulator (for example, gp 120, 100 ηg/0.1 ml) and a similar group was injected with 0.1 ml buffer every 3 days for 4 weeks. Tumor area was monitored over this time as described above. Mice receiving the modulator showed no further growth in the tumor area or showed some shrinkage of the tumor mass over the 4 week dosing regimen. Alternatively, mice receiving the control injection continued to show increased growth in the tumor mass, and were sacrificed before the end of the 4 week period Mice injected with colon tumor lines SCID mice were injected with two colon tumor lines as described above, with tumors appearing at about 4 to 6 weeks post-injection. On confirmation of tumor growth, one group of mice (2 of each colon tumor type) were injected with modulator (Nef peptide) at 20 ηg/0.1 ml and a second similar group was injected with 0.1 ml buffered solution once a week for 4 weeks. Tumor area was monitored over this time as described above. Mice receiving the modulator showed significant shrinkage of the tumor mass over the 4 week dosage regimen. Alternatively, mice receiving the control injection continued to show growth in the tumor mass and were sacrificed before the end of the 4 weeks.

What is claimed is:

1. A composition of matter containing, as an active agent, a peptide consisting of the amino acid sequence NAA-CAWLEAQ (SEQ ID No: 7) in a pharmaceutically acceptable carrier.

2. The composition of matter of claim 1 wherein the peptide is contained in liposomes or microspheres.

3. The composition of mailer of claim 1 in a liquid form.

4. The composition of matter of claim 1 in wherein the peptide is on a solid support.

5. The composition of matter of claim 2 wherein the peptide is a targeting liposome.

6. The composition of matter of claim 2 wherein the peptide is in a microsphere.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
       (A) LENGTH: 21 base pairs
       (B) TYPE: nucleic acid
       (C) STRANDEDNESS: single
       (D) TOPOLOGY: unknown (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO: 1:

CCTAGAAGAA TAAGACAGGG C                      21

(2) INFORMATION FOR SEQ ID NO: 2:

(i) SEQUENCE CHARACTERISTICS:
       (A) LENGTH: 22 base pairs
       (B) TYPE: nucleic acid
       (C) STRANDEDNESS: single
       (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

CACTACTTGA AGCACTCAAG GC                    22

(2) INFORMATION FOR SEQ ID NO: 3:

(i) SEQUENCE CHARACTERISTICS:
       (A) LENGTH: 34 base pairs
       (B) TYPE: nucleic acid
       (C) STRANDEDNESS: single
       (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

CCTCTTCAGC TACCACCGCT TGAGAGACTT ACTC          34

(2) INFORMATION FOR SEQ ID NO: 4:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

TGACTAAAAT GGTCTGAGG                                 19

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

GAAGAAGGAG GTGGAAACGA CG                             22

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

AAGTGCTGGT GAGAGTCTAG C                              21

(2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 7:

Asn Ala Ala Cys Ala Trp Leu Glu Ala Gln
1               5              10

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 8:

Ala Leu Ala Glu Thr Cys Asn Ala Trp Ala
1               5                  10

(2) INFORMATION FOR SEQ ID NO: 9:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 9:

Gly Arg Ala Phe Tyr Thr Thr
1               5

(2) INFORMATION FOR SEQ ID NO: 10:

(i) SEQUENCE CHARACTERISTICS:
        (A) LENGTH: 30 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 10:

Ser Thr Leu Leu Leu Asn Gly Ser Leu Ala Glu Glu Glu Val Val Il
1               5                  10                  15
Arg Ser Glu Asn Phe Thr Asp Asn Ala Lys Thr Ile Ile Val
            20                  25                  30

(2) INFORMATION FOR SEQ ID NO: 11:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (iii) HYPOTHETICAL: NO

```
    (iv) ANTI-SENSE: NO (xi) SEQUENCE DESCRIPTION: SEQ ID NO: 11:

Gly Arg Ala Phe Tyr Thr Thr Lys Tyr
1               5
```